United States Patent [19]

Latge et al.

[11] Patent Number: 5,193,382

[45] Date of Patent: Mar. 16, 1993

[54] CLOGGING INDICATOR FOR CONTROLLING SODIUM QUALITY

[75] Inventors: Christian Latge, Aix-en-Puce; Guy Lemercier, Le Puy Sainte Reparade; Bernard Puech, Pertuis; Georges Jullien, Lyon, all of France

[73] Assignee: Commissariat A L'Energie Atomique, Paris, France

[21] Appl. No.: 735,784

[22] Filed: Jul. 25, 1991

[30] Foreign Application Priority Data

Jul. 30, 1990 [FR] France .................. 90 09675

[51] Int. Cl.$^5$ ............................................. G01N 11/00
[52] U.S. Cl. .................................................. 73/61.74
[58] Field of Search ............... 73/61.74, 61.76, 61.46

[56] References Cited

U.S. PATENT DOCUMENTS

| | | | |
|---|---|---|---|
| 2,997,874 | 8/1961 | Billuris et al. | 73/61.74 |
| 3,200,637 | 8/1965 | Ballou et al. | 73/61.74 |
| 3,343,401 | 9/1967 | Delisle | 73/61.76 X |
| 3,390,571 | 7/1968 | Roach et al. | 73/61.74 |
| 3,624,709 | 11/1971 | Potrek | 73/61.74 |
| 3,672,209 | 6/1972 | Roach et al. | 73/61.74 X |
| 3,996,790 | 12/1976 | Murase et al. | 73/61.76 |
| 4,178,795 | 12/1979 | Nagai | 73/61.74 X |
| 4,274,280 | 6/1981 | Nei et al. | 73/61.74 |
| 4,297,873 | 11/1981 | Nei et al. | 73/61.74 |

FOREIGN PATENT DOCUMENTS

1093224 11/1967 United Kingdom .

Primary Examiner—Hezron E. Williams
Assistant Examiner—Joseph W. Roskos
Attorney, Agent, or Firm—Pearne, Gordon, McCoy & Granger

[57] ABSTRACT

The clogging indicator makes it possible to continuously measure the purity of sodium circulating in the circuits of a fast neutron reactor without requiring the dismantling or completely changing the indicator should the measuring section becomes clogged. The clogging indicator essentially includes a bypass pipe comprising one coaxial external section (8) and one coaxial internal section (9). A measuring head (10) is mounted and able to move between these two sections and is mainly composed of at least one thermoelement (24) and one mobile grid (22) causing the measuring section to vary and thus the measured flow so as to favor uncloggings and the dissolving of any impurities crystallized during the measurements. This unit is completed by the other main elements of the clogging indicator in an elongated longitudinal body and surrounded by a thermic exchanger (11) for cooling the sodium.

7 Claims, 6 Drawing Sheets

CLOGGING INDICATOR FOR CONTROLLING SODIUM QUALITY

FIELD OF THE INVENTION

The invention concerns control of the quality of sodium circulating in the circuits of an installation and in particular in test circuits and the circuits of fast neutron nuclear reactors.

BACKGROUND OF THE INVENTION

In fast neutron nuclear reactors, the liquid coolant of the primary circuit, which sends the calories provided by the fission reaction to the heat exchanger, is liquid sodium. So that such reactors may function properly, it is necessary to continuously monitor the quality of the sodium circulating in these circuits. In particular, it is essential to monitor any possible precipitation of sodium oxide and hydride crystals into the sodium itself. Having regard to the fact that the solubility of these impurities decreases when the temperature of the sodium drops, it is possible, by creating a cooling point around a calibrated hole of a sodium circuit, to provoke crystallization of any possible impurities. Such a crystallization causes the flow of sodium to reduce, which may be measured simultaneously with the temperature. Thus, a correlation has been established between the clogging temperatures of the sodium and the oxide and hydride percentages contained in the latter.

This principle is used by clogging indicators which determine the clogging temperature below which sodium oxide and hydrides start to precipitate.

Generally speaking, a clogging indicator is connected in parallel on a main pipe at the terminals of a diverter so that the flow of the branch circuit connection section is independent of any pressure fluctuations in the main pipe. The indicator itself mainly includes a contracted section where clogging is caused by cooling and where the evolution of the temperature and the flow of sodium in the branch circuit connection is simultaneously monitored. To this effect, a ventilation heat exchanger surrounds the clogging indicator which includes as a measuring member at least two thermoelements and two flowmeters. A filter may be placed at the inlet of the clogging indicator. At the outlet of the indicator, the sodium derived from the branch circuit connection or bypass pipe is remixed with the sodium of the main pipe.

In circuits carrying liquid sodium, the unclogging of the contracted measuring section is an extremely long operation and is often impossible when said section is completely clogged by impurities. In fact, in the event of a complete clogging, it is not possible to unclog the orifices without dismantling this contracted section, and even when clogging is only partial, after a normal functioning measurement, the time for dissolving the crystallized impurities is extremely long.

The object of the invention is to resolve these drawbacks by providing a clogging indicator, the unclogging of the orifices of the measuring section not requiring any dismantling or complete change of the device and making it possible to reduce the time for dissolving any impurities after each measurement.

SUMMARY OF THE INVENTION

To this effect, the main object of the invention is to provide a clogging indicator for controlling the quality of sodium circulating in a main pipe and including:

branch circuit connection means for measuring the flow of one portion of the sodium in the main pipe in a measuring conduit of pipes;

means for cooling the branch circuit connection pipe including a thermic heat exchanger for cooling the sodium at a constant speed;

a measuring head comprising at least two thermoelements for measuring the temperature of the sodium in a measuring section of the branch circuit connection pipe;

adjusting, measuring and recording means for determining an unclogging temperature.

According to the invention, the measuring head is able to move axially with respect to the branch circuit connection pipe inside a housing and includes a measuring chamber formed by a cylindrical wall comprising in its lower portion an annular grid able to be housed around the central tube of the branch circuit connection pipe, and, in its upper portion, a seat on which a mobile hemispherical valve is able to be supported, said valve being provided with measuring thermoelements and able to move axially inside a cylindrical bell rendered integral with the cylindrical wall of the measuring chamber and comprising holes enabling the gas or liquid sodium to be removed to an evacuation pipe and an upper stop on which the annular shoulder of the valve in a high position takes support, thus allowing, by lifting up said valve, to have the measuring chamber communicate with the evacuation pipe and then to free the annular grid of the central tube of the branch circuit connection pipe.

So as to facilitate the sliding and guiding of the measuring head inside the housing, the latter preferably comprises guiding bosses outside the cylindrical wall.

The relative axial movement of the grid with respect to firstly the central tube of the branch circuit connection pipe and secondly the valve with respect to the measuring chamber enables the measuring head to obtain three different positions:

in one first position, known as the normal operating position, the valve is pressed onto the seat of the measuring chamber and the annular grid is disposed around the central tube of the branch circuit connection pipe forming a contracted section for passage of the liquid sodium;

in a second position, known as a drain position, the annular grid is placed around the central tube of the branch circuit connection pipe, but the valve is lifted up from its seat, which, especially when operating the clogging indicator, makes it possible to move the gas and drain sodium towards the evacuation pipe;

in a third position, known as the unclogging position, the valve is lifted up as far as possible, thus freeing the grid of the central tube of the branch circuit connection pipe and making it possible to increase the flow of the hot sodium at the level of the grid, which favors the unclogging of the calibrated holes of said grid.

With the aim of obtaining a good efficiency of cooling of the branch connection pipe, the clogging indicator of the invention benefits from a compactness of the structure around the branch connection pipe.

In fact, this pipe is preferably a double annular pipe with a longitudinal axis and comprising one internal pipe and one external pipe, the latter being surrounded by a thermic exchanger.

An inert body may be inserted on the axis of the internal branch connection pipe downstream of the measuring head so as to favor heating of the deviated sodium.

The compactness of the clogging indicator of the invention is improved by means of a design using the mounting of concentric pipes and integrating the means ensuring the various functions. Thus, the indicator includes a longitudinal body surrounding the double annular pipe forming the branch circuit connection pipe and including at one first upper extremity the mobile head and at a second extremity a channel for admitting the sodium, a distribution chamber, a filter for the sodium, one inlet of the flowmeter branch circuit connection pipe, one diverter for adjusting the measured flow, a sodium outlet collecting pipe serving as a mixer and a second flowmeter placed in said collecting branch connection pipe so as to measure the flow of sodium circulating in the main pipe.

DETAILED DESCRIPTION OF THE PREFERRED EMBODIMENTS

Figure 1:
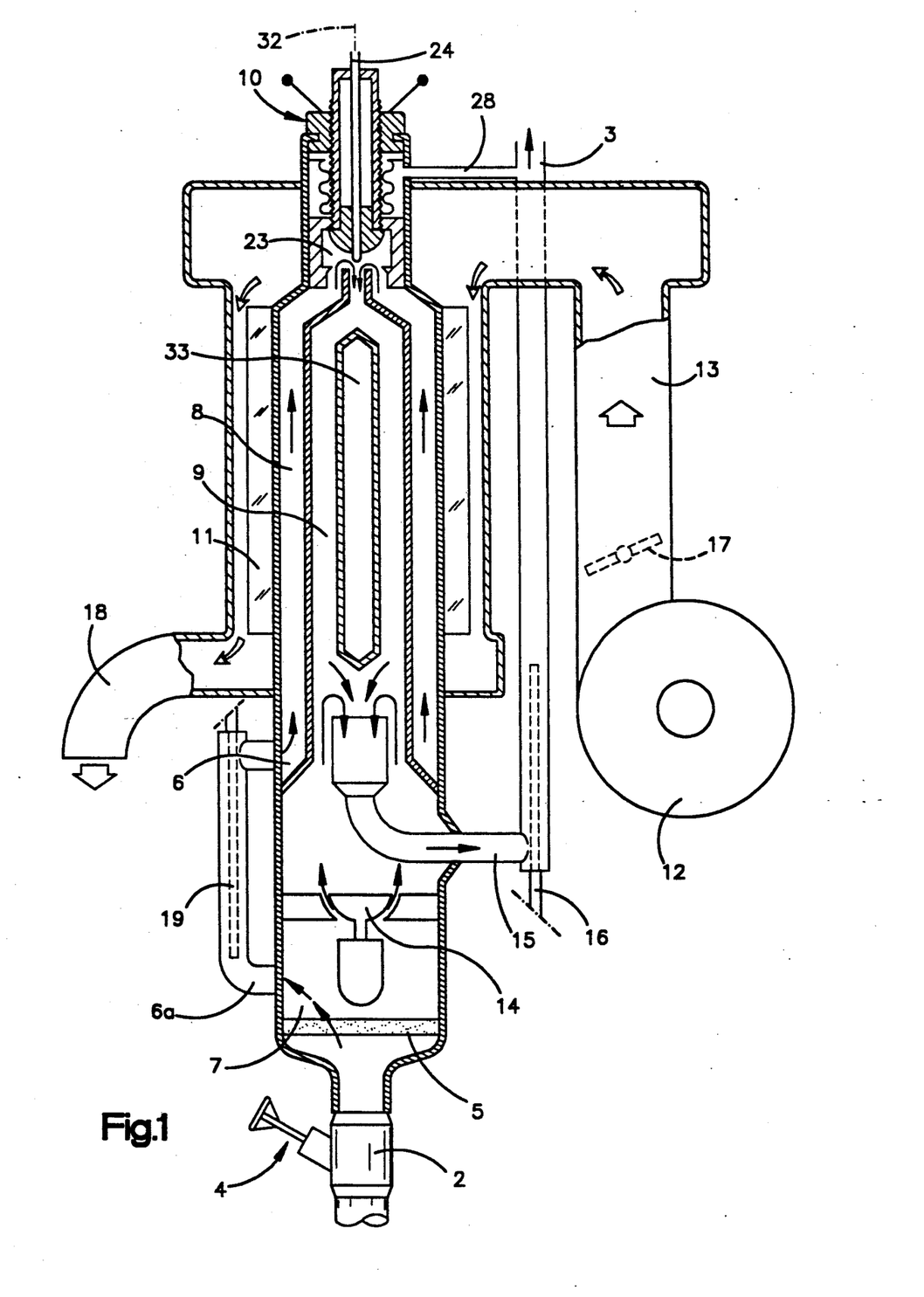
FIG. 1 is a diagrammatic section of the clogging indicator of the invention.

With reference to FIG. 1, the clogging indicator of the invention principally includes sodium drain means placed on one main pipe between one inlet 2 and one outlet 3, and means for adjusting, measuring, heating and cooling the unit.

By chronologically following the path traversed by the sodium, the inlet 2 of the sodium is provided with a valve 4 for stopping and adjusting the general flow of sodium. A filter 5 is advantageously placed at the inlet of the clogging indicator. This filter 5 may be formed of a metal cloth retaining the solid impurities or metallic particles contained in the sodium.

The dump means are mainly constituted by a distribution pipe 7 and a branch circuit connection pipe 6a whose inlet 6a is placed immediately downstream of the filter 5. A first flow measurement is made by a flowmeter 19 at the start of this branch circuit connection pipe 6. So as to improve the compactness of the unit, this first flowmeter 19 is a glove finger type flowmeter, which makes it possible to change it without breaking the imperviousness of the branch circuit connection pipe 6.

Again with the aim of obtaining compactness, the branch circuit connection pipe is preferably embodied in the form of a double annular pipe constituted by one external pipe 8 surrounding one internal pipe 9. The measuring chamber 23 of the measuring head 10 is situated between these two pipes, said measuring head thus being downstream of the external pipe 8 and upstream of the internal pipe 9.

The measuring head 10 shall be described subsequently in detail with reference to FIGS. 3A, 3B and 3C. In simplest terms, it is mobile along the vertical axis 32. The external pipe is surrounded by a preferably vane type sodium/air thermic exchanger 11 fed with air by a ventilator 12 by means of a pipe 13. An inert body 33 is situated at the center of the internal branch circuit connection pipe 9 forcing a larger amount of deviated sodium to come into contact with the common wall of the two concentric pipes 8 and 9, thus contributing in heating the deviated sodium.

The sodium not deviated by the branch circuit connection pipe 6 passes into a deviator 14 functioning at constant pressure so as to adjust the sodium flow to be controlled. A collecting pipe 15 is placed downstream of the deviator 14 and downstream of the internal portion 9 of the branch circuit connection pipe 6. It is equipped with a second flowmeter 16 for measuring the total flow of the sodium circulating in the main pipe. The deviated sodium and the sodium derived from the deviator 14 is reinjected into this collecting pipe 15 and is removed via the outlet 3.

The ventilator 12 may be completed by an adjustment sliding valve 17 placed downstream of the latter in the pipe 13. This sliding valve may be motorized and makes it possible to adjust the flow of air according to the temperatures of the cycle of the clogging measurements to be carried out. The fresh air thus enters via the upper portion of the indicator, that is at the level of the measuring head 10, and comes out heated at the level of the lower portion of the exchanger 11 via the evacuation pipe 18. This cooling circuit is designed in such a way that, should the ventilator 12 stop functioning, natural convection does not start inside the cooling circuit.

Figure 2:
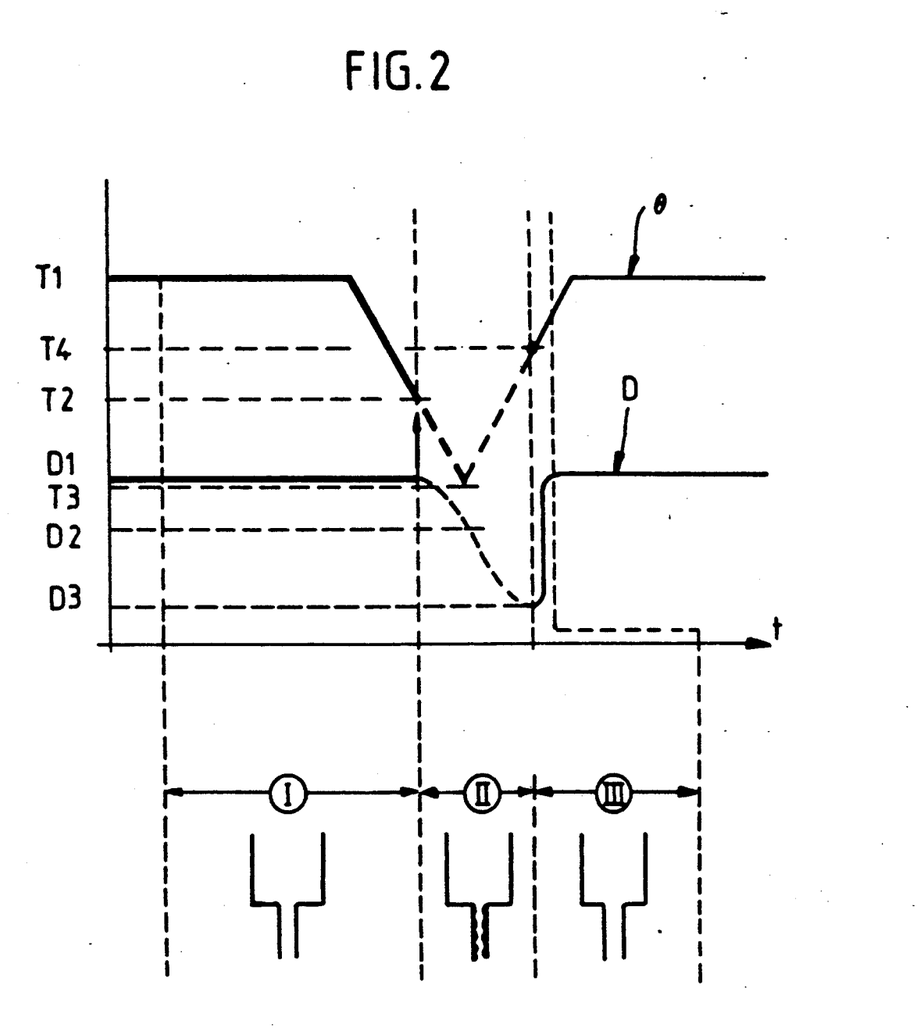
FIG. 2 is a graph relating to the functioning of the clogging indicator of the invention.

With reference to the curves of FIG. 2, the functioning of the clogging indicator of the invention is as follows. The upper curve marked represents, according to the time involved, the temperature in the measuring section of the branch circuit connection pipe at the location of the measuring head. Correspondingly, the lower curve marked D represents, according to the time involved, the sodium flow through the branch circuit connection pipe and thus through the measuring section. The two curves are completed by three diagrams symbolizing the presence or absence of crystals in the sodium, again according to the time involved.

In the zone I, the temperature of the deviated sodium is T1 representing that of the sodium in the main pipe, namely about 500° C. The sodium is then cooled at constant speed when it passes into the external portion of the branch circuit connection pipe. This cooling may be adjusted by means of the sliding valve 17 of FIG. 1, such as at the speed of 3° C./mn. The temperature is preferably recorded.

The cooling of the temperature at constant speed is extended until it reaches the temperature T2 corresponding to the start of the formation of crystals in the branch circuit connection pipe. T2 constitutes the clogging temperature. Conjointly, at the start of the zone II, the flow in the branch circuit connection pipe starts to gradually abate according to the growth of the formation of crystals in the contracted measuring section, as shown on the lower diagram of zone II.

The temperature continues to decrease in this zone 2 as far as the temperature T3 corresponding to a flow D2 having a value of about 80% of the nominal flow D1, namely 96 l/hr. The adjustment sliding valve is then closed and the circulation of air is stopped. The temperature in the branch circuit connection pipe and in the measuring section starts to rise. The flow continues to decrease owing to the inertia of the crystallization phenomenon until it reaches the minimum flow D3 corresponding to a temperature T4 slightly higher than the clogging temperature T2 where the crystal dissolution phenomenon starts. This phenomenon continues for a time symbolized by the zone III and the flow quickly recovers its nominal value D1. Conjointly, the temperature also reverts to the nominal temperature T1.

Once a cycles of measurements has been completed, a second cycle may be started.

Figure 3A:
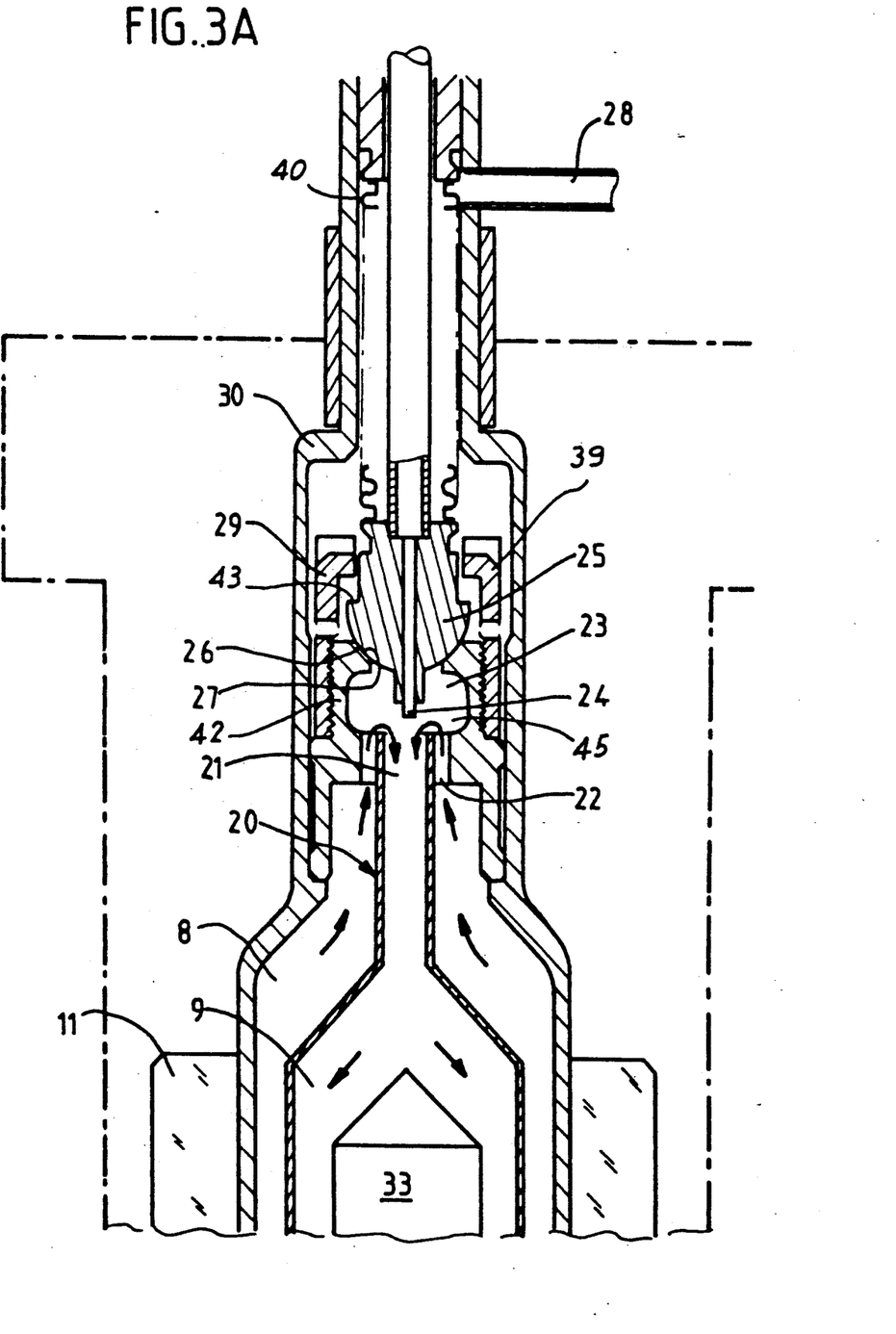
FIGS. 3A, 3B and 3C are detailed cutaway views of the measuring head of the clogging indicator of the invention and shown in its three main positions.

With reference to FIG. 3, the measuring head is shown in detail in its operating position, that is when the measuring section is contracted. This figure also shows the external pipe 8 and the internal pipe 9 of the branch circuit connection pipe, as well as the upper portion of the vane sodium/air exchanger 11. Inversion of the direction of circulation of the sodium occurs around a contracted tube 20 extending the partition between the external 8 and internal 9 pipes of the branch circuit connection pipe. The section is contracted by an annular grid 22 which is calibrated by holes so as to impose a stable flow of sodium and is placed at the end of the external portion 8 of the branch circuit connection pipe around the extremity 21 of the central tube 20. The change of direction of circulation of the sodium is effected around the extremity 21 of the tube in a measuring chamber 23 into which the measuring thermoelements 24 open. Only one of these thermoelements 24 has been shown on this figure for the sake of simplification. However, three thermoelements may be housed against one another in the measuring head by being grouped into a triangle.

The thermoelement 24 shown on this FIG. 3A is placed in a hemispherical valve 25 inside which it slides. The hemispherical valve 25 takes support via a spherical surface 26 on a seat 27 integral with the annular grid 22. The thermoelement 24 has its extremity relatively close to the extremity 21 of the tube 20 so as to be located in the middle of the flow of deviated sodium and whose temperature is representative of the latter, as indicated by the small arrows symbolizing the circulation of the latter. The entire unit is mounted inside a housing 30 prolonging the external wall of the partition delimiting the external portion 8 of the branch circuit connection pipe and the vanes of the heat exchanger 11.

Means for the translation moving of the measuring head may either be electromagnets or a hydraulic or pneumatic system or even a nut/screw system. The translation sliding and guiding of the measuring head 10 inside the housing 30 are provided by guiding bosses 37 placed outside the cylindrical wall 42 of the measuring chamber 23.

Figure 3B:
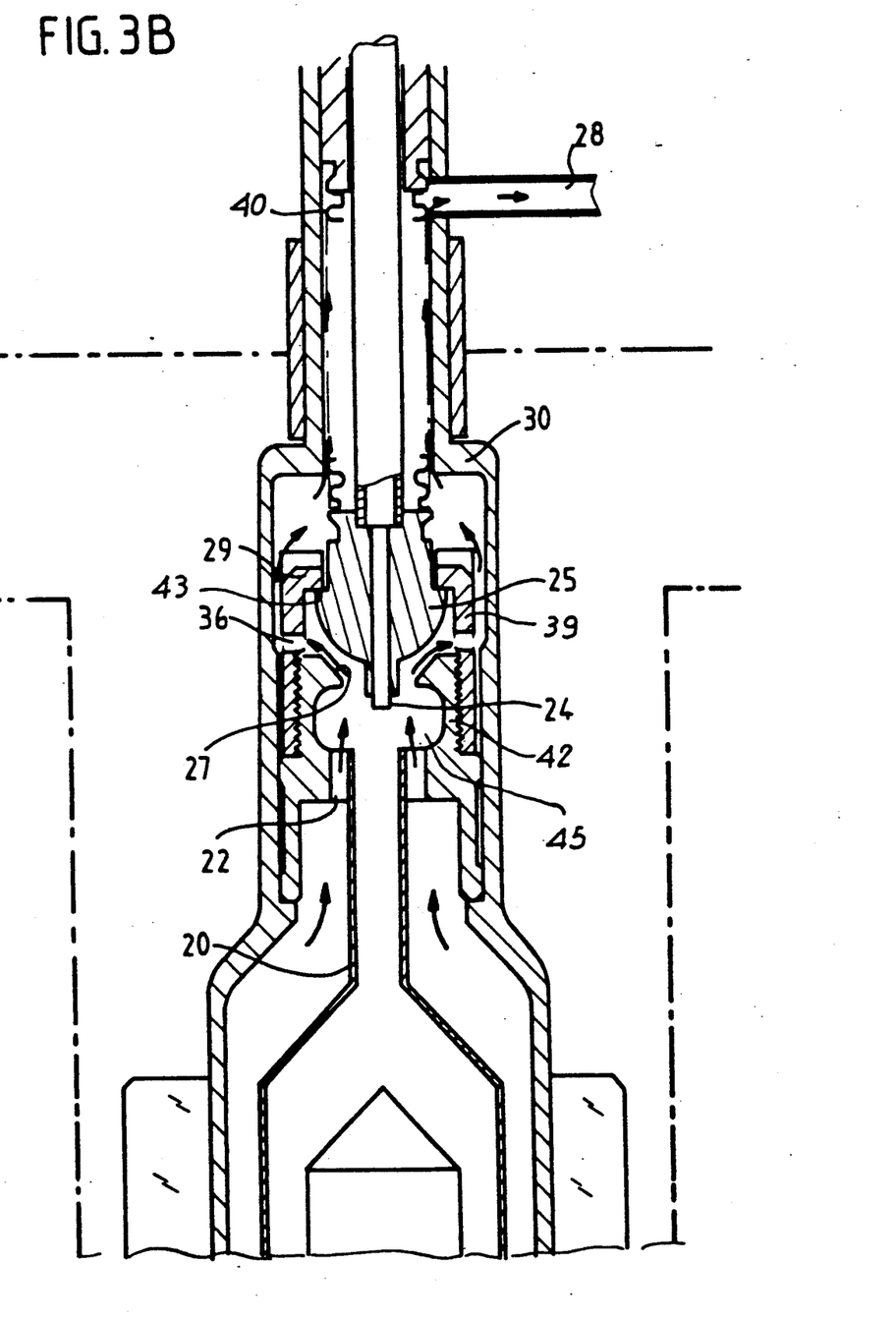

As shown on FIG. 3B, the measuring head is in its intermediate position. The unit formed from the thermoelement 24 and the valve 25 is lifted up. The valve 25 is no longer in support on the seat 26 and thus enables the sodium or gas to pass towards the evacuation pipe 28 connected to the main outlet 3. This evacuation pipe 28 serves as a drain.

This FIG. 3B shows that the measuring chamber 23 enables the sodium to pass towards the internal branch circuit connection pipe 9, but also allows the sodium or gas to be removed through the holes and the annular gaps between the housing 30 and a cylindrical bell 39 and then along a pair of bellows 40 towards the evacuation pipe 28 which may also be connected to an expansion flask. This position, known as a drain position, is used to make use of the clogging indicator.

Figure 3C:
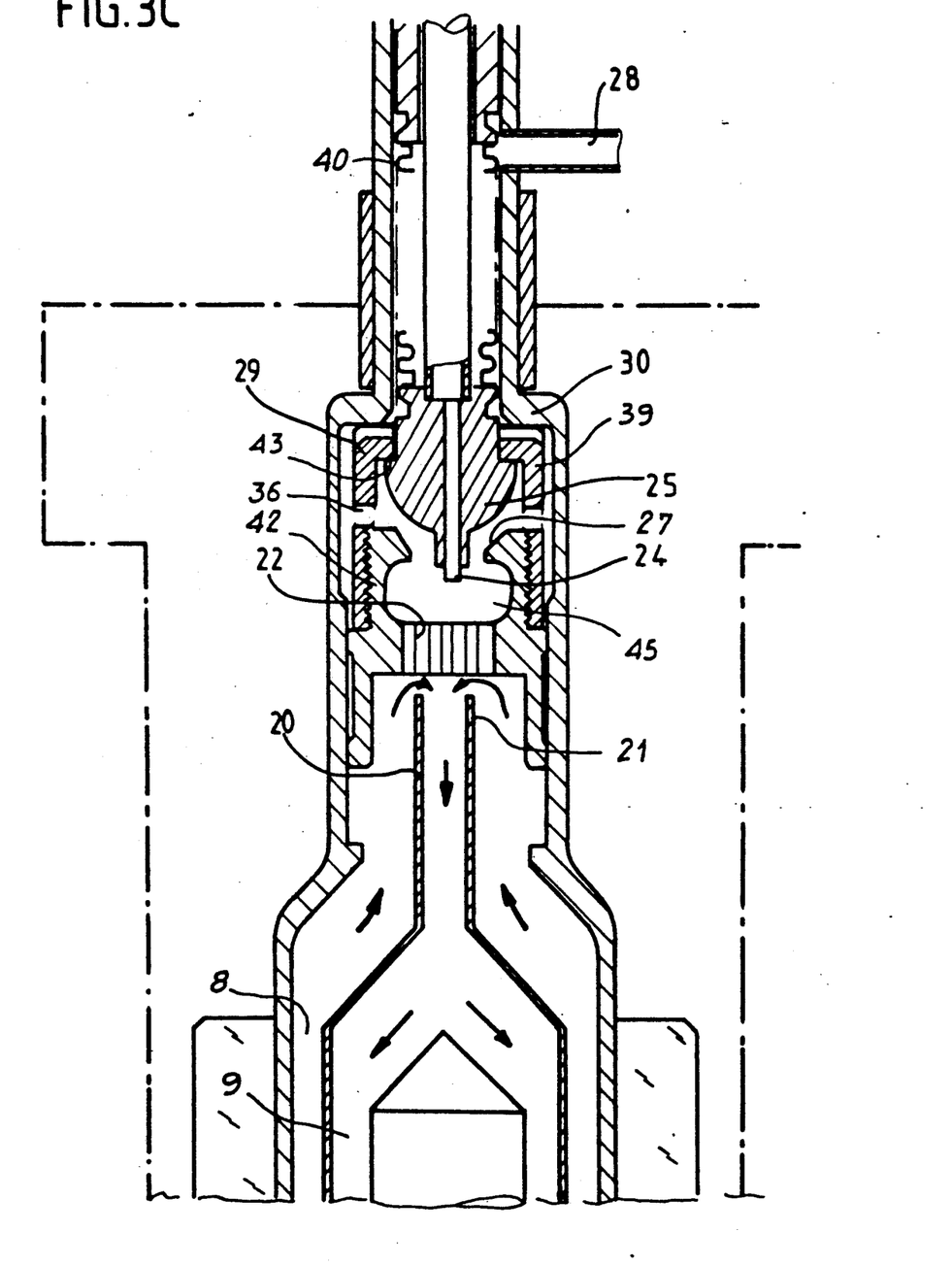

FIG. 3C shows the measuring head in its unclogging position, in other words the measuring section is wide. So as to obtain this position, the unit, including the annular grid 22 integral with the seat 27 by means of the cylindrical wall 42 and the valve 25 which bears the thermoelements 24, is pushed back as far as possible.

During the backward movement of the valve 25, the shoulder 43 of the latter comes into contact with the stop 29 of the cylindrical bell 39 integral with the cylindrical wall 42 of the measuring chamber 45 and lifts up the mobile unit of the measuring head 10.

In this position, the grid is freed from the extremity 21 of the tube 20, thus allowing for a greater flow of the sodium circulating in the branch circuit connection pipe 8 towards the internal pipe 9 and thus dissolving the oxide and hydride crystals formed at the level of the annular grid 22. This position thus enables the active portion of the clogging indicator to be unclogged, the measuring section being located at the inlet of the measuring chamber 23, and thus allows for manual releases with the aid of electromagnet systems. Any possible full clogging may thus be prevented without changing and dismantling the clogging indicator.

The application of the latter is relatively simple as the evacuation pipe 28 serves as a drain for the gas during filling.

In a secondary circuit of a fast neutron reactor, the sodium oxide and hydride percentages may be extremely high. Thus, it is extremely advantageous to have, along with the clogging indicator of the invention, a retractable contracted section making it possible to free the orifices clogged with impurities and subject the latter to a sodium current so as to dissolve these as quickly as possible when the temperature rises. The clogging measuring cycles may be controlled by a microprocessor, the temperature and flow being recorded at the same time.

This clogging indicator makes it possible to control the sodium by means of measurements carried out in the temperature interval of between 110° C. and 550° C. at the level of the contracted measuring section with a flowrate of 120 1/hr.

Figure 4:
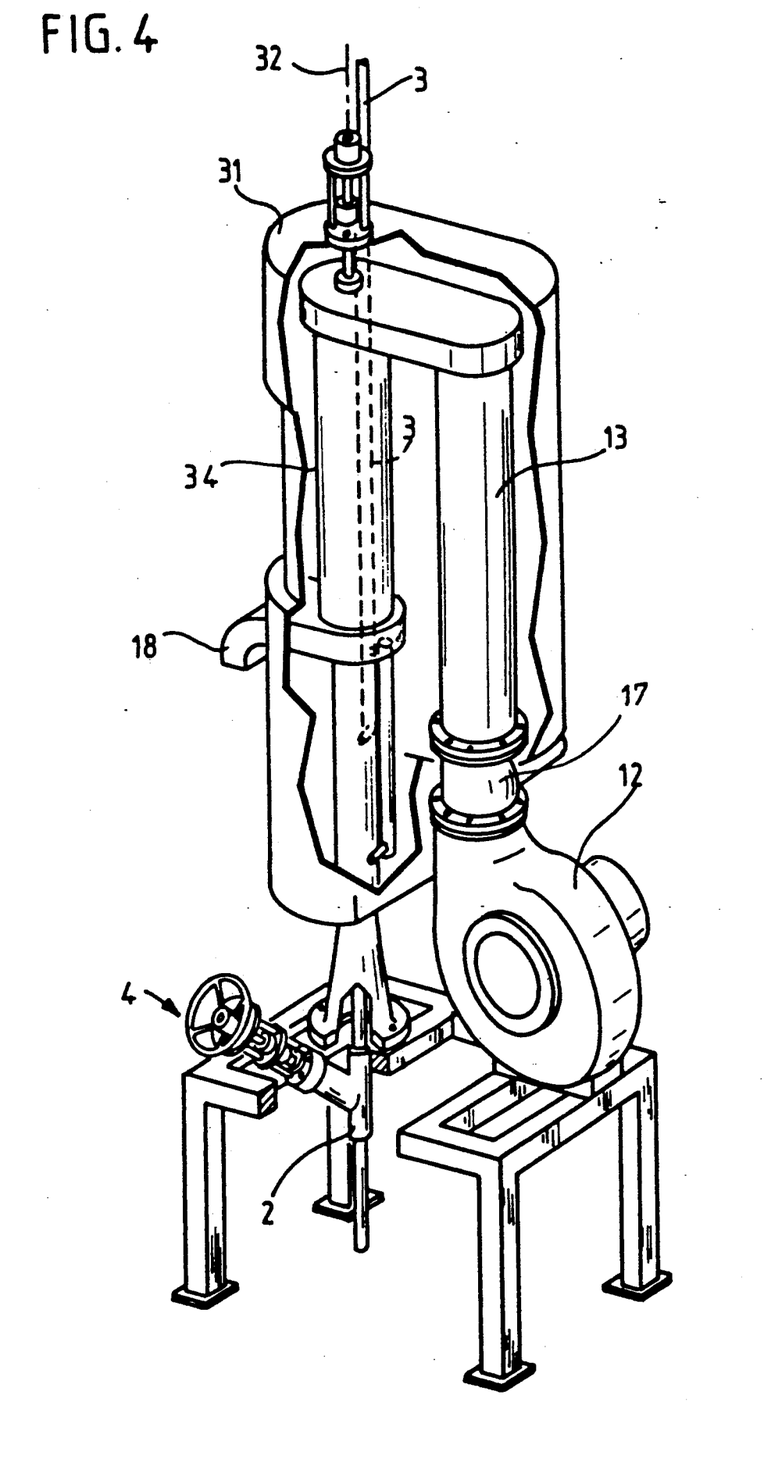
FIG. 4 is a diagrammatic view of the cavalier projection of the clogging indicator of the invention.

With reference to FIG. 4, the clogging indicator of the invention, apart from the stop valve 4 placed at the inlet 2 and the ventilator 12, is surrounded by a heat insulated chamber 31. This chamber is shown as a section in order to illustrate that the left portion placed in the axis of the inlet 2 is regrouped around the vertical axis 32 in a vertical body 34. This portion mainly includes the filter, the divertor, the branch circuit connection pipe with its internal and external portions and, at its upper portion, the measuring head. The right portion mainly includes the pipe 13 connected to the sliding lock 17 and the ventilator 12 for cooling the sodium.

When the divertor is integrated, as well as the outlet collecting pipe in the vertical body 34, the temperature of the outer wall of the lower portion of the device is uniform, even though temperature differences of about 400° exist in the device upstream of this outlet collecting pipe. Secondly, in the upper portion, the longitudinal thermic gradient in the cooled zone is borne extremely easily, this zone having a regular cylindrical shape. Thus, one can readily understand that the compactness of the clogging indicator of the invention thus reduces spatial requirements and the thermic gradients inherent to the functioning of this type of device.

Several technical characteristics of one embodiment of the clogging indicator of the invention may be given:
  the valve 4 for stopping and adjusting the inlet 2 may be a manual valve making it possible to adjust the flow measured by the outlet flowmeter 16 ;

the flowmeters 15 and 16 may be magnetic flow distortion type flowmeters;

the divertor 14 may be a calibrated valve maintaining a constant flow in the branch circuit connection pipe;

in the case where three thermoelements are used in the measuring head, the first is used for adjustment, the second for recording the measurement, and the third ensures measurement or adjustment redundancy;

measuring and recording devices are connected to the flowmeters and thermoelements;

for applications in fast neutron reactors, the range of temperatures used is between 160° C. and 550° C., and the temperature at the level of the contracted measuring section may fall to 110° C. without causing the sodium to freeze up.

The clogging measurement is a cyclic function and may be controlled by a microprocessor.

WHAT IS CLAIMED IS:

1. Clogging indicator for controlling the quality of sodium circulating in a main pipe and including:
   means for diverting and measuring the flow of one portion of the sodium of the main pipe into a branch circuit connection pipe;
   means for cooling the branch circuit connection pipe and including a thermic exchanger to cool the sodium at a constant speed;
   a measuring head including at least two thermoelements for measuring the temperature of the sodium in a measuring section of the branch circuit connection pipe;
   adjustment, measuring and recording means for determining a clogging temperature; result wherein the measuring head is able to move axially with respect to the branch circuit connection pipe inside a housing and includes one measuring chamber formed by one cylindrical wall comprising in its lower portion an annular grid able to be housed around a central tube of the branch circuit connection pipe and, in its upper portion, a seat on which a mobile hemispherical valve is able to be supported provided with measuring thermoelements and able to move axially inside a cylindrical bell rendered integral with the cylindrical wall of the measuring chamber and comprising holes for the passage of the gas or liquid sodium towards an evacuation pipe and one upper stop on which an annular shoulder of the valve takes support in an upper position, thus lifting up said valve so as to have the measuring chamber communicate with the evacuation pipe and then free the annular grid of the central tube of the branch circuit connection pipe.

2. Indicator according to claim 1, wherein, so as to facilitate the sliding and guiding of the measuring head inside the housing, the latter comprises guiding bosses outside the cylindrical wall.

3. Indicator according to claim 1 or 2, wherein the annular grid moves with respect to the central tube of the branch circuit connection pipe and wherein the valve moves with respect to the measuring chamber enabling the measuring head to obtain three different positions:
   in one first position known as a normal operating position, the valve is pressed onto the seat of the measuring chamber and the annular grid is disposed around the central tube of the branch circuit connection pipe, thus forming a contracted section for passage of the liquid sodium;
   in one second position known as a drain position, the annular grid is in place around the central tube of the branch circuit connection pipe, but the valve is lifted up from its seat which, especially when the clogging indicator is operating, makes it possible to remove the gas and drain sodium towards the evacuation pipe;
   in a third position known as the unclogging position, the valve is lifted up as far as possible, thus freeing the annular grid of the central tube of the branch circuit connection pipe and enabling the flow of hot sodium at the level of the annular grid to be increased, which favors the unclogging of the calibrated holes of said annular grid.

4. Indicator according to claim 1, wherein the branch circuit connection pipe is made up of one double annular pipe with a longitudinal axis comprising one internal pipe and one external pipe, the latter being surrounded by a thermic exchanger.

5. Indicator according to claim 1, wherein an inert body is placed inside the internal portion of the branch circuit connection pipe.

6. Clogging indicator according to claim 1, wherein further comprising a vertical body surrounding the double annular pipe forming the branch circuit connection pipe and including the mobile head at one first upper extremity and at a second lower extremity:
   the sodium inlet;
   a filter;
   a branch circuit connection pipe inlet including a first flowmeter;
   a diverter for adjusting the measured flow;
   a sodium collecting pipe serving as a mixer; and
   a second flowmeter placed in said collecting pipe for measuring the flow of the sodium circulating in the main pipe.

7. Clogging indicator according to claim 6, further comprising a heat-insulating casing surrounding the body and the heat exchanger, as well as a ventilation pipe so as to feed the latter with air, this ventilation pipe being connected to a ventilator.

* * * * *

UNITED STATES PATENT AND TRADEMARK OFFICE
CERTIFICATE OF CORRECTION

PATENT NO.   : 5,193,382
DATED        : March 16, 1993
INVENTOR(S)  : Christian Latge et al.

It is certified that error appears in the above-identified patent and that said Letters Patent is hereby corrected as shown below:

Column 7, Claim 1, line 35, delete "result".

Column 8, Claim 6, line 37, delete "wherein".

Signed and Sealed this

Thirtieth Day of November, 1993

Attest:

Attesting Officer

BRUCE LEHMAN

Commissioner of Patents and Trademarks